US009636301B2

(12) United States Patent
Weber (10) Patent No.: US 9,636,301 B2
(45) Date of Patent: May 2, 2017

(54) IN VITRO RELEASE ASSAY FOR LIPOSOME ENCAPSULATED VINCRISTINE

(71) Applicant: ARBUTUS BIOPHARMA CORPORATION, Burnaby (CA)

(72) Inventor: Thomas Philip Weber, Surrey (CA)

(73) Assignee: ARBUTUS BIOPHARMA CORPORATION, Burnaby, BC (CA)

( * ) Notice: Subject to any disclaimer, the term of this patent is extended or adjusted under 35 U.S.C. 154(b) by 0 days.

(21) Appl. No.: 14/649,481

(22) PCT Filed: Dec. 4, 2013

(86) PCT No.: PCT/US2013/073125
§ 371 (c)(1),
(2) Date: Jun. 3, 2015

(87) PCT Pub. No.: WO2014/089216
PCT Pub. Date: Jun. 12, 2014

(65) Prior Publication Data
US 2015/0297519 A1 Oct. 22, 2015

Related U.S. Application Data (60) Provisional application No. 61/733,059, filed on Dec. 4, 2012.

(51) Int. Cl.
| | |
|---|---|
| *A61K 31/439* | (2006.01) |
| *A61K 9/127* | (2006.01) |
| *G01N 33/94* | (2006.01) |
| *G01N 30/02* | (2006.01) |

(52) U.S. Cl.
CPC .......... *A61K 9/1275* (2013.01); *A61K 31/439* (2013.01); *G01N 30/02* (2013.01); *G01N 33/94* (2013.01)

(58) Field of Classification Search
CPC .................................................... A61K 31/439
See application file for complete search history.

(56) References Cited

U.S. PATENT DOCUMENTS

2006/0008909 A1  1/2006 Cullis et al.

OTHER PUBLICATIONS

Barbet et al (Biochimica et Biophysica Acta (BBA)—Biomembranes vol. 772, Issue 3, May 30, 1984, pp. 347-356).*
Embree, et al., "Valildation of a high-performance liquid chromatographic assay mehtod for quantification of total vincristine sulfate in human plasma following administration of vincristine sulfate liposome injection", Journal of Pharmaceutical and Biomedical Analysis 16, 675-687 (1997).
Johnston, et al., "Therapeutically optimized rates of drug release can be achieved by varying the drug-to-lipid ratio in liposomal vincristine formulations", Biochimica et Biophysica Acta 1758, 55-64 (2006).

(Continued)

*Primary Examiner* — Benjamin Packard
(74) *Attorney, Agent, or Firm* — Viksnins Harris & Padys PLLP (57) ABSTRACT

The present invention provides a novel in vitro release assay for the accurate, reproducible quantitation of vincristine sulfate release from liposomes.

15 Claims, 5 Drawing Sheets

(56) References Cited

OTHER PUBLICATIONS

Nakamura, et al., "Designing a novel in vitro drug-release-testing mehtod for liposomes prepared by pH-gradient method", International Journal of Pharmaceutics, vol. 430 (1), 381-387 (2012).

Patent Cooperation Treaty, International Searching Authority, Search Report and Written Opinion for PCT/US2013/073125, 11 pages, Feb. 24, 2014.

Shan, et al., "Preferential extravasation and accumulation of liposomal vincristine in tumor comparing to normal tissue enhances antitumor activity", Cancer Chemother Pharmacol. 58(2), 245-255 (2006).

Webb, et al., "Preclinical pharmacology, toxicology and efficacy of sphingomyelin/cholesterol liposomal vincristine for therapeutic treatment of cancer", Cancer Chemother Pharmacol. 42(6), 461-70 (1998).

* cited by examiner

IN VITRO RELEASE ASSAY FOR LIPOSOME ENCAPSULATED VINCRISTINE

CROSS-REFERENCE TO RELATED APPLICATION(S)

This patent application claims the benefit of priority of U.S. application Ser. No. 61/733,059, filed Dec. 4, 2012, which application is herein incorporated by reference.

BACKGROUND

Liposomes are well established nanoparticles that can enhance the efficacy of therapeutically active drugs by improving the plasma distribution and pharmacokinetics of the drugs over non-encapsulated forms (e.g., Weinstein, Liposomes: From Biophysics to Therapeutics, (Ostro, M. J., ed.), Marcel Dekker, Inc., N.Y., pp. 277-338, (1987). For example, Vincristine Sulfate Liposome Injection (VSLI) is a liposome formulation of the anti-cancer therapeutic vincristine sulfate encapsulated in sphingomyelin-cholesterol liposomes, which provides greater efficacy than standard vincristine sulfate injection USP (VSI). Clinical trials have also shown that VSLI facilitates dose intensification by significantly extending vincristine's circulation half-life compared to non-encapsulated vincristine. The liposome provides the mechanism for delayed drug release and the liposome size allow the drug to accumulate in cancer tissues by extravasation (Webb et al., Cancer Chemother. Pharmacol 42:461-470, 1998; Shan et al., Cancer Chemother. Pharmacol 58:245-255, 2006). These features translate into improved clinical benefit over the standard VSI.

Consistency of product quality and performance is a key parameter of all drug products. During development and optimization of liposome drug formulations, a variety of physical and chemical tests commonly performed on liposome drug products (e.g., solubility, particle size, osmolality, homogeneity) have historically provided reasonable evidence of consistent performance. However, alterations in formulation composition, manufacturing process, equipment and batch sizes may require studies in human healthy volunteers, increasing the time and cost of the getting the drug on the market.

More recently, in vitro release testing has been employed as a means to evaluate release characteristics that reflect in vivo bioavailability. In vitro drug release testing measures, the release of the active ingredient from the drug product in controlled laboratory environment and should simulate the physiological environment of human plasma. It involves subjecting the dosage form to a set of conditions that will induce drug release and quantitating the amount of drug released under those conditions. During drug development, the test can be used to assess differences in formulations, to predict the timeframe of active ingredient release, and in vivo behavior. As a tool for quality control, the test can be used to assess conformance of a batch to pre-determined criteria at time of manufacture and to assess the long-term stability and release of the active ingredient. In vitro release assays can also assist in quality control for certain scale-up and post-approval changes (SUPAC).

One of the key challenges, however, is developing an in vitro drug release assay that discriminates between different liposome compositions and physiochemical characteristics and how they affect in vivo drug profiles. Although human plasma has been employed as a medium for in vitro release, as a means to simulate the in vivo environment, the practical difficulties of biosafety and inherent lot-to-lot variability of plasma makes this an unacceptable option for routine product testing. Thus, there remains a need for reliable in vitro methods that provide a means for assuring that each batch of the same liposome product will have drug release characteristics that are substantially identical.

SUMMARY OF THE INVENTION

Liposomes are chemically complex nanoparticles and the analysis of drug retention properties are not easily predictive. The present invention provides a novel in vitro release assay for the accurate, reproducible quantitation of vincristine sulfate release from liposomes.

In one aspect the invention features a method of determining the in vitro release rate of vincristine from vincristine sulfate liposome vincristine injection (VSLI). In the method VSLI is added to an incubation solution comprising 1-butanol and phosphate buffered saline (PBS) to a final concentration of 1-butanol between about 2.7% and about 2.8% (v/v). The incubation solution containing the VSLI is then heated for a period of at least about 72 hours at about 37° C.±0.1° C. At two or more time points during the incubation period an aliquot of the incubation solution containing the VSLI is removed, and the released (free) vincristine in each aliquot is separated from the VSLI by filtering each aliquot through a membrane which retains particles with $D_{25}$ of 70 nm and $D_{90}$ of 170 nm. The amount of released vincristine in the filtrate from each aliquot is then determined by high performance liquid chromatography and the in vitro release rate of the vincristine from the VSLI is determined.

In one embodiment, the final the concentration of 1-butanol in the incubation solution is 2.75%. In one embodiment, the VSLI is diluted by about 1:21 in the incubation solution. In certain embodiments, the pH of the incubation solution is between about 7.0 and about 7.4, and is preferably about 7.4. In one embodiment, the incubation solution is equilibrated to 37° C.±0.1° C. prior to the addition of the VSLI. In one embodiment, the incubation solution containing the VSLI is heated for about 96 hours.

In certain embodiments, an aliquot is removed from the incubation solution containing the VSLI at two or more time points selected from the group consisting of about 0.5 hours, about 2 hours, about 4 hours, about 6 hours, about 24 hours, about 72 hours and about 96 hours. In certain embodiments, at least two aliquots are removed at each time point. In one embodiment, two aliquots are removed at each time point. In another embodiment, each aliquot is about 0.5 mL.

In certain embodiments, the aliquots are filtered through a membrane having a nominal molecular weight limit of between about 10,000 and 100,000 daltons. In other embodiments, the nominal molecular weight limit of the membrane is between about 30,000 and 100,000 daltons. In one embodiment, the nominal molecular weight limit of the membrane is about 100,000 daltons.

In certain embodiments, each aliquot is filtered at a centrifugal force of about 12,000×g for about 20 to about 30 minutes at 20° C.

In certain embodiments, the membrane is pretreated with a passivation solution comprising bovine serum albumin, polyethylene glycol and PBS. In one embodiment, the passivation solution comprises 5% bovine serum albumin, 5% polyethylene glycol and PBS. In other embodiments, the is pretreated with the passivation solution for about 15 to about 25 hours at room temperature and rinsed with water prior to filtration of the aliquot.

In other embodiments, the method includes determining the total vincristine sulfate concentration in the incubation solution. In one embodiment, the total vincristine sulfate concentration is released from the VSLI by the addition of methanol to the incubation solution.

In certain embodiments, the filtrate from each aliquot is to HPLC at about 297 nm. In certain embodiments, the HPLC flow rate is about 1.0 mL/min. In one embodiment, the limit of quantitation for vincristine is about 0.116 µg/mL.

In certain embodiments, between about 30% to about 50% of the vincristine is released from the VSLI within about 0.5 hours. In other embodiments, about 45% to about 75% of the vincristine is released from the VSLI within about 6.0 hours. In other embodiments, about 65% to about 85% of the vincristine is released from the VSLI within about 6.0 hours. In one embodiment, greater than about 80% of the vincristine encapsulated in the VSLI is released within 72 hours. In another embodiment, greater than about 80% of the vincristine encapsulated in the VSLI is released within 96 hours.

In certain embodiments, the VSLI comprises a concentration ratio of about 0.1/1.0 to about 0.2/2.0 vincristine sulfate to lipid. In other embodiments, the concentration of vincristine sulfate in the VSLI is about 0.1 mg/mL to about 0.5 mg/mL. In other embodiments, the concentration of vincristine sulfate in the VSLI is about at about 0.15 mg/mL to about 0.2 mg/mL. In one embodiment, the concentration of vincristine sulfate in the VSLI is about at about 0.16 mg/mL.

In certain embodiments, the liposomes in the VSLI comprise between about 75/25 mol %/mol sphingomyelin/cholesterol to 30/50 mol %/mol % sphingomyelin/cholesterol. In other embodiments, the liposomes in the VSLI comprise about 70/30 mol %/mol sphingomyelin/cholesterol to 40/45 mol %/mol % sphingomyelin/cholesterol. In one embodiment, the liposomes in the VSLI comprise approximately 55/45 mol %/mol % sphingomyelin/cholesterol. In still other embodiments, the liposomes have a mean diameter of about 90-125 nm.

In one aspect the invention features a vincristine sulfate liposomal injection solution assayed according to a method described herein.

In one aspect the invention features a batch of vincristine sulfate liposomal injection solution assayed according to a method described herein.

In one aspect the invention features a commercially marketable liposomal vincristine sulfate solution prepared according to a method described herein.

Other features and advantages of the invention will be apparent from the following detailed description and the claims.

DETAILED DESCRIPTION

In vitro release (IVR) assays for liposomal drug products are described that can be used to evaluate the release characteristics of the encapsulated drug, and to discriminate between liposomal drug products batches with significantly different formulations or compositions. The drug release data generated using the disclosed IVR assays aligns well with in vivo pharmacokinetic and biodistribution results of liposomes and are suitable for use on a routine basis for product release and stability testing in a quality control environment. Thus, the IVR assays disclosed herein are particularly useful as a routine Quality Control (QC) check to identify product lots with gross manufacturing defects.

DEFINITIONS

Unless specifically noted otherwise, all technical and scientific terms used herein have the standard definitions commonly understood by one of ordinary skill in the art of therapeutic and pharmaceutical science.

The singular form "a," "an," and "the" include plural reference unless the context clearly dictates otherwise.

The terms "comprise" and comprising" are used in the inclusive, open sense, meaning that additional elements may be included.

The term "about", particularly in reference to a given quantity or number, is meant to encompass deviations of plus or minus five percent.

"Liposome" "vesicle" and "liposome vesicle" will be understood to indicate structures having lipid-containing membranes enclosing an aqueous interior. The structures may have one or more lipid membranes unless otherwise indicated, although generally the liposomes will have only one membrane. Such single-layered liposomes are referred to herein as "unilamellar". Multilayer liposomes are referred to herein as "multilamellar".

A "standard" therapeutic agent, or "free" therapeutic agent, refers to a therapeutic agent that is not liposome-encapsulated. Usually, a drug is presumed to be "standard or "free" unless specified otherwise. A standard vinca alkaloid in free form may still be present in combination with other reagents, however, such as other chemotherapeutic compounds, a pharmaceutical carrier, or complexing agents, i.e. as used herein the term only specifically excludes lipid formulations of the vinca alkaloids.

Mathematically, the term "correlation" refers to the interdependence between quantitative or qualitative data or relationship between measurable variable and ranks. From a biopharmaceutical standpoint, as used herein, correlation refers to the relationship between in vitro release characteristics and in vivo bioavailability parameters.

The term "IVIV", as used herein, is a predictive mathematical model describing the relationship between an in vitro property of a drug encapsulated liposome dosage form and a relevant in vivo response. Generally, the in vitro property is the rate or extent of drug migration or release from the interior of a liposome and reflects the membrane permeability attributes of a liposome. It also reflects in vivo release characteristics responsible for the improved biodistribution and pharmacokinetics of drug encapsulated liposomes.

The term "batch" refers to a specific quantity of drug or other material produced according to a single manufacturing order during the same cycle of manufacture and intended to have uniform character and quality within specified limits.

The term "drug product" refers to a finished dosage form (e.g., liposome) that contains a drug substance (e.g., vincristine), generally, but not necessarily, in association with one or more other ingredients.

The term "drug substance" refers to an active ingredient that is intended to furnish pharmacological activity or other direct effect in the diagnosis, cure, mitigation, treatment, or prevention of a disease, or to affect the structure or any function of the human body, but does not include intermediates used in the synthesis of such ingredient.

The term "formulation" refers to the listing of the ingredients and quantitative composition of the dosage form.

The term "drug release" refers to the diffusion or migration of a drug, encapsulated in a liposome from the liposome interior thereby allowing the drug to be distributed into the body where it may exert its' pharmacological effect.

A "sterile" composition or container, as used herein, is free of viable microbes as determined using the USP sterility test. (See, "The United States Pharmacopeial Convention: 2008).

Vincristine Sulfate

Vincristine sulfate is a member of a vinca alkaloid family originally isolated from the periwinkle plant (*Catharanthus roseus*). Vincristine Sulfate has cell-cycle specific anticancer activity. The vinca alkaloid binds to tubulin, altering tubulin polymerization leading to metaphase arrest, inhibition of cell mitosis, and cell death. As a cell cycle specific agent its' therapeutic response is advanced by liposome encapsulation which maintains extended drug levels. Prolonged exposure of cells to vincristine (and other cell cycle specific drugs) has been shown to enhance in vitro cytotoxicity of the drug (Bfurris et al, JNCI 84; 1816-1826, 1992; Georgiadis et al., Clin Cancer Res 3:449-454, 1997; Jackson and Bender, Cancer Res 39:4346-4349, 1979).

Vincristine sulfate is commonly isolated as a 1:1 sulfate salt. It is a hygroscopic, white to slightly yellowish crystalline powder that is soluble in water. It has a molecular weight of 923.04 (salt form)/824.98 (base form) and a molecular formula of $C_{46}H_{56}N_4O_{10} \cdot H_2SO_4$. The chemical name for vincristine sulfate is 22-oxovincaleukoblastine and it has the following chemical structure:

Vincristine sulfate is prescribed as vincristine sulfate injection USP (e.g., as a 1 mg/mL solution) and is also known as leurocristine sulfate, Kyocristine, vincosid, vincrex, oncovin, Vincasar PFS®, is commercially available from any of a number of sources.

Liposomes

The liposome carrier component of the present invention is comprised of sphingomyelin and cholesterol liposomes injection (SCLI). The ratio of sphingomyelin to cholesterol present in the liposome may vary, but generally is in the range of from 75/25 mol %/mol sphingomyelin/cholesterol to 30/50 mol % mol % sphingomyelin/cholesterol. In one embodiment, the liposome composition comprise about 70/30 mol % mol sphingomyelin/cholesterol to 40/45 mol % mol % sphingomyelin/cholesterol. In another embodiment, the liposome compositions comprise approximately 55/45 mol % mol % sphingomyelin/cholesterol. In still another embodiment the liposome compositions comprise about 60/40 mol % mol % sphingomyelin/cholesterol.

In certain embodiments, additional lipids may be present in the formulations, for example, to prevent lipid oxidation or to attach ligands onto the liposome surface. Generally, the inclusion of other lipids will result in a decrease in the sphingomyelin/cholesterol ratio.

The sphingomyelin/cholesterol liposomes used in the present invention can be multilamellar or unilamellar. Suitable methods for preparing the liposomes include, but are not limited to, sonication, extrusion, high pressure/homogenization, microfluidization, detergent dialysis, calcium-induced fusion of small liposome vesicles, thin film evaporization, and ether-infusion methods, all of which are well known in the art. For example, a variety of methods are available for preparing liposomes as described in, e.g., Szoka, et al., Ann. Rev. Biophys. Bioeng., 9:467 (1980), U.S. Pat. Nos. 4,186,183, 4,217,344, 4,235,871, 4,261,975, 4,485,054, 4,501,728, 4,774,085, 4,837,028, 4,946,787, 5,543,152, 6,723,338, WO 91/17424, Deamer and Bangham, Biochim. Biophys. Acta, 443:629 634 (1976); Fraley, et al., Proc. Natl. Acad. Sci. USA, 76:3348 3352 (1979); Hope, et al., Biochim. Biophys. Acta, 812:55 65 (1985); Mayer, et al., Biochim. Biophys. Acta, 858:161 168 (1986); Williams, et al., Proc. Natl. Acad. Sci., 85:242 246 (1988), the text Liposomes, Marc J. Ostro, ed., Marcel Dekker, Inc., New York, 1983, Chapter 1, and Hope, et al., Chem. Phys. Lip., 40:89 (1986), all of which are incorporated herein by reference.

Following liposome preparation, the liposomes can be sized to achieve the desired particle size range using standard methods well-known in the art (e.g., see U.S. Pat. No. 6,723,338). Typically liposomes which can be used in the VSLI preparations described herein have a size range of about 0.05-0.5 microns (50-500 nm), 0.2-0.4 microns (200-400 nm), about 0.1-0.4 microns (100-400 nm), about 0.05-0.2 (50-200 nm) or about 0.5 (500 nm) to about 0.15 microns (150 nm). In certain embodiments, the liposomes have a particle size having a mean particle diameter of about 50 nm, about 60 nm, about 70 nm, about 80 nm, about 90 nm, about 100 nm, about 105 nm, about 110 nm, about 115 nm, about 120 nm, about 130 nm, about 140 nm, about 150 nm, about 160 nm, 170 nm, about 180 nm, about 190 nm, or about 200 nm. In one embodiment, the average particle size is between 90 and 125 nm with the preferred average particle size about 107.5 nm, where 25% ($D_{25}$) of the particle size distribution is not less than 70 nm and where 90% ($D_{90}$) of the distribution has a particle size of not more than 170 nm.

The sphingomyelin/cholesterol liposomes function as the liposome component used in the VSLI preparations described herein and are manufactured so that the liposome interior has a low pH. During the constitution process VSI, having a low pH, and SCLI, having a low pH, are diluted in a buffer of a higher pH whereby the final pH of the external VSLI solution is about physiologically neutral. The result is the creation of a pH gradient across the lipid membrane in which the pH is lower in the interior core of the liposomes than the exterior surrounding solution. Such gradients are achieved according to known methods (e.g., U.S. Pat. No.

6,723,338). For example, gradients can be achieved by formulating the liposomes in the presence of a buffer with a pH between about 2 and about 6, a pH between about 3 and about 5, and then subsequently transferring the liposomes to a higher pH, for example, of about 7.0 to about 7.5. In one embodiment, the liposomes have an interior pH of about 4.0. Any number of dilution buffers can be used, such as sodium phosphate. In one embodiment the buffer has a pH of 8-10, preferably 9.0, so that the final diluted external liposome solution when mixed with VSI and SPLI will have a physiologic neutral pH.

Prior to use in the preparation of VSLI according to the methods described herein, the SPLI liposomes can be stored at refrigerated conditions for substantial periods of time prior to drug encapsulation and constitution of VSLI for administration to a patient. Alternatively, the liposomes can be dehydrated, stored and then rehydrated prior to use in accordance with well-known methods (See, e.g., U.S. Pat. Nos. 5,077,056 or 5,736,155).

VSLI Preparation

VSLI is prepared with strict aseptic techniques, for example, in a biological safety cabinet or by established pharmacy safety procedures for the preparation of sterile injectable formulations and hazardous drugs. Procedures for handling and disposal of anticancer drugs must be strictly followed (NIOSH Alert: Preventing occupational exposure to antineoplastic and other hazardous drugs in healthcare settings. 2004. U.S. Department of Health and Human Services, Public Health Service, Centers for Disease Control and Prevention, National Institute for Occupational Safety and Health, DHHS (NIOSH) Publication No. 2004-16; OSHA Technical Manual, TED 1-0.15 A, Section VI: Chapter 2. Controlling Occupational Exposure to Hazardous Drugs. OSHA, 1999; American Society of Health-System Pharmacists. ASHP guidelines on handling hazardous drugs. Am J Health-Syst Pharm. (2006) 63:1172-1193; Polovich M, White J M, Kelleher L O (eds.) 2005. Chemotherapy and biotherapy guidelines and recommendations for practice (2nd. ed.) Pittsburgh, Pa.: Oncology Nursing Society).

Constituted VSLI can be prepared by methods, such as those described in U.S. Pat. Nos. 6,723,338 and 7,887,836; co-pending U.S. Application No. 61/728,378; the FDA-approved label for VSLI (www.accessdata.fda.gov; Reference ID: 3172211, 2012), and the Examples.

VSLI

The VSLI produced according to the methods described herein appears as a white to off-white, translucent suspension, essentially free of visible foreign matter and aggregates. Typically, greater than about 95%, about 96%, about 97%, about 98% or more of the vincristine sulfate is encapsulated in the liposomes.

The VSLI produced according to the methods described herein contains total impurities of less than about 4.0%, 3.5%, 3.4%, 3.2%, 3.1% or 3.0%. In some embodiments, the VSLI contains less than about 2.0%, 1.8%, 1.7%, 1.6%, 1.5%, 1.4% or 1.3% N-desformylvincristine.

Generally, the VSLI produced according to the methods described herein contains vincristine sulfate at about 0.1 mg/mL to about 0.5 mg/mL. In certain embodiments, the vincristine sulfate is present at about 0.15 mg/mL to about 0.2 mg/mL. In one embodiment, the vincristine sulfate is present at about 0.16 mg/mL. In one embodiment, the VSLI contains 5 mg vincristine sulfate, 500 mg mannitol, 73.5 mg sphingomyelin, 29.5 mg cholesterol, 36 mg sodium citrate, 38 mg citric acid, 355 mg sodium phosphate, and 225 mg sodium chloride.

In Vitro Release Assay (IVR)

The release rate of vincristine from VSLI is determined in vitro according to the following steps, VSLI is added to an incubation solution comprising 1-butanol and phosphate buffered saline, to a final concentration of 1-butanol after addition of between about 2.7% and about 2.8% (v/v);

The incubation solution containing the VSLI is incubated for at least about 72 hours at about 37° C.±0.1° C.;

At two or more time points during the incubation, aliquots of the incubation solution containing the VSLI are removed;

Each aliquot is filtered through a membrane having the ability to retain particle sizes distributed between $D_{25}$ of 70 nm and $D_{90}$ of about 170 nm in order to separate released vincristine from the VSLI;

The amount of released vincristine in the filtrate of each aliquot removed at each time point is determined by high performance liquid chromatography; and The amount of released vincristine at each time point is indicative of the release rate of vincristine from the VSLI.

(i) Incubation

In the methods disclosed herein, the release-promoting agent 1-butanol ("butanol") is included in the incubation solution. Butanol, a short-chain n-alcohol that is miscible with water at concentrations below approximately 10% (v/v), was chosen as the release media based on a number of parameters including reproducibility, sensitivity to osmolality and suitability for use in a Quality Controlled environment. It is commercially available in highly pure form, easy to prepare, has low volatility and is not biohazardous.

In the methods of the invention, the incubation solution contains between about 2.0% and about 3.0% butanol. In some embodiments, the incubation solution contains about 2.0%, about 2.25%, about 2.4%, about 2.5%, about 2.6%, about 2.75%, about 2.8%, about 2.9% or about 3.0% butanol. In certain embodiments, the incubation solution contains between about 2.7% and about 2.8% 1-butanol. In one embodiment, the incubation solution contains about 2.75% 1-butanol.

In certain embodiments, the pH of the incubation solution is between about 7.0 and about 7.4. In some embodiments, the pH of the incubation solution is about 7.1, about 7.2 about 7.3 or about 7.4. In one embodiment, the pH of the solution is 7.4 (±0.01).

In one embodiment, the incubation solution contains at least a 1:10 dilution of VSLI:release medium. In one embodiment, the incubation solution contains at least a 1:20 dilution of VSLI:release medium. In another embodiment, the incubation solution contains a 1:21 dilution of VSLI:release medium.

In one embodiment, the incubation solution is prewarmed to equilibrate the temperature to 37° C. (±0.1°) prior to addition of the VSLI. In another embodiment, the incubation solution containing the VSLI is gently agitated (e.g., about 70 rpm) during the time course of the assay.

In the methods of the invention, the incubation solution containing the VSLI is heated at 37° C. (±0.1°) for a time period which results in the release of at least about 80% of the vincristine from the VSLI. In some embodiments, the solution containing the VSLI and release promoting agent is incubated at 37° C. (±0.1°) for least about 24 hours, at least about 36 hours, at least about 48 hours, at least about 72 hours, at least about 96 hours. In one embodiment, the time course is about 72 hours. In another embodiment, the time course is about 96 hours.

During the time course of the incubation, one or more aliquots of the incubation solution containing the VSLI are removed at two or more different time points. In certain embodiments, at least two aliquots are removed at each time point. In certain embodiments, one or more aliquots are removed at two or more time points selected from about 0.5 hours, about 2 hours, about 4 hours, about 6 hours, about 24 hours, about 72 hours and about 96 hours. In one embodiment, one or more aliquots are removed at about 0.5 hours, about 2 hours, about 4 hours, about 6 hours, about 24 hours, about 72 hours and about 96 hours.

The volume of each aliquot is sufficient to quantitate the amount of free (released) vincristine after filtration. In certain embodiments, the limit of quantitation (LOQ) for vincristine is about equivalent to about 1.5% of the target concentration of total vincristine for HPCL analysis. In one embodiment, the LOQ is about 0.116 μg/mL vincristine. In certain embodiments, each aliquot is between about 0.2 and about 1.0 mL. In one embodiment, each aliquot is about 0.5 mL.

(ii) Ultrafiltration

The free (released) vincristine is separated from the encapsulated vincristine by ultrafiltration. Suitable filtration devices are commercially available which allow the retention of the liposome particles. In some embodiments, the filtration device allows retention of particles of liposome particles whose $D_{25}$ is not less than (NLT) 70 nm and $D_{90}$ is not more than (NMT) 170 mm. In certain embodiments, the ultrafiltration device has a cut off of at least about 10,000 MW to about 100,000. Examples of suitable filtrations devices include the Microcon YM-30 and Microcon YM-100 or their equivalent. In some embodiments, the filtration device allows vincristine recovery of at least about 95%, at least about 96%, or at least about 97%. In one embodiment, greater than 97% vincristine is recovered after filtration.

In some embodiments, the ultrafiltration device is pretreated with a passivation solution to block the nonspecific binding of vincristine to the surface of the filtration membrane. In certain embodiments, the passivation solution contains bovine serum albumin, polyethylene glycol and PBS. In one embodiment, the passivation solution contains about 5% bovine serum albumin. In one embodiment, the passivation solution contains 5% polyethylene glycol. In another embodiment, the passivation solution contains 5% bovine serum albumin and 5% polyethylene glycol.

In some embodiments, the filters are pretreated with the passivation solution for at least about 8 hours, at least about 9 hours, at least about 10 hours, at least about 11 hours, at least about 12 hours, at least about 13 hours, at least about 14 hours, at least about 15 hours, to about 24 hours. In one embodiment, the filters are pretreated with the passivation solution for about 15 to about 24 hours.

In some embodiments, the filters are pretreated with the passivation solution at room temperature (about 18-22° C.). In some embodiments, the passivation solution is removed prior to filtration of the VSLI sample. In some embodiments, the passivation solution is removed by rinsing the filter with water, preferably purified water, prior to use. In certain embodiments the filter is rinsed two or more times. In one embodiment, the filter is rinsed three times with purified water prior to use.

Each aliquot of the incubation solution containing VSLI is filtered at between about 10,000×g and about 13,000×g at about 18-22° C. for about 20-40 minutes. In some embodiments, each aliquot is filtered at about 12,000×g. In one embodiment, each aliquot is filtered at about 12,000×g at 20° C. for about 30 minutes.

In other embodiments, the IVR assay includes instructions to identify membrane failures and to confirm accuracy of the results.

(iii) High Performance Liquid Chromatography

Following separation of free (released) vincristine from liposomes by ultrafiltration, the filtrate is analyzed by reverse-phase HPLC for vincristine content. In some embodiments, the HPLC procedure is based on the USP vincristine assay method for VSI. In certain embodiments, the HPLC used in the in vitro assay uses a larger injection volume. In one embodiment, the injection volume is about 40 μL. In certain embodiments, the flow rate is reduced. In one embodiment, the flow rate is about 1.0 mL/min. In certain embodiments, HPLC is conducted under isocratic conditions. In one embodiment, the isocratic conditions comprise a pre-mixed mobile phase comprised of 30% of a first mobile phase component comprising diethylamine (DEA) solution and 70% of a second mobile phase component comprising methanol. In one embodiment, the first mobile phase component comprises about 1.67% v/v DEA at a pH of about 7.5.

(iv) Determination of Encapsulated Vincristine

The amount of vincristine that remains encapsulated at one or more time points during the incubation period may also be determined. In one embodiment, a sample of VSLI incubated according the IVR methods described herein is spiked with additional 1-butanol to a final concentration of about 4% to induce maximum drug release, filtered and subjected to HPLC to determine the amount of free (released) vincristine. In another embodiment methanol can be used to induce maximum drug release. The amount of encapsulated vincristine is then determined by the difference between the amount of free (released) vincristine in the spiked sample and the amount in an un-spiked sample taken at the same time point. In preferred embodiments, spiked sample is taken between about 6 and 24 hours.

Dosage and Administration

VSLI can be used to treat any type of cancer including primary, relapsed and refractory cancers. The patient or subject treated with the VLSI may be a variety of animals, including humans, non-human primates, avian species, equine species, canine species, feline species, bovine species, swine, lagomorphs, rodents, and the like. In certain embodiments, the VSLI is used to treat cancers of the blood and lymphatic systems including, but not limited to, lymphomas, leukemias and myelomas. In certain embodiments, the VSLI is used to treat tumors including, but not limited to neuroblastomas and brain cancers.

VSLI may be admixed with a pharmaceutically acceptable diluent suitable for intravenous administration to the patient (e.g., dextrose, sodium chloride) which may be provided, for example in a pre-filled, sterile container (glass bottle, plastic bottle or plastic bag). In some embodiments, the volume of the patients calculated dose is removed from an infusion bag and replaced with the calculated volume of the constituted VSLI solution into an infusion bag, for example, where the final volume of the infusion container will be 100 mL. In one embodiment, the pharmaceutically acceptable diluents is of 5% Dextrose Injection or 0.9% Sodium Chloride Injection.

The VSLI can be used as a single agent or in combination with other chemotherapeutic agents, such as cyclophosphamide, doxorubicin and/or prednisone. In one embodiment, the VSLI is administered along with as cyclophosphamide, doxorubicin and prednisone as a liposomal CHOP formulation ("lipo-CHOP"). In another embodiment, the VSLI is co-administered with at least one additional anti-tumor agent. In another embodiment, the additional anti-tumor agent is an anti-tumor monoclonal antibody, such as Oncoly™, Rituxan™, or Bexxar™. In another embodiment, the additional anti-tumor agent is an antisense drugs or an anti-tumor vaccine. In another embodiment, the VSLI is co-administered with a prophylactic or therapeutic treatment for neurotoxicity, such as gabapentin (Neurontin™).

Typically, the VSLI is prepared within about 24 hours of administration to the patient and is stored at room temperature (15° C. to 30° C.,) or refrigerated (2-8° C.).

The VSLI is administered to the patient systemically by intravenous delivery. In one embodiment, the VSLI is administered by intravenous infusion over a period of, e.g., about 30 minutes, about 45 minutes, about 60 minutes, about 90 minutes or longer.

Typically, the VSLI is administered periodically, e.g., once every 7-28 days. In certain embodiments, the VSLI is administered once every 3, 5, 7, 10, 14, 21 or 28 days. In one embodiment, the VSLI is administered by intravenous infusion every 14 days. In another embodiment, the VSLI is administered by intravenous infusion every 7 days. As used herein, each administration of VSLI is considered one "course" of treatment.

The amount of VSLI administered per dose will depend on a number of factors, such as the medical history of the patient, the use of other therapies, and the nature of the disease (e.g., first line, relapsed or refractory cancer). Typically, the VSLI prepared according to the methods described herein is administered at a dosage of about 1.4 to about 2.4 mg/m$^2$. In certain embodiments, the VSLI is administered at a dose of about 1.5 mg/m$^2$, about 1.8 mg/m$^2$, about 2.0 mg/m$^2$, 2.1 mg/m$^2$, 2.2 mg/m$^2$, 2.3 mg/m$^2$ or 2.4 mg/m$^2$ (i.e., mg vincristine per m$^2$ body surface area). In one embodiment, the VSLI is administered at a dose of 2.25 mg/m$^2$ by intravenous infusion over about 60 minutes once every 7 days.

In other embodiments, the dose of VSLI may be temporarily interrupted and/or reduced during treatment. For example, in one embodiment, the dosage of VSLI administered to a patient portraying a Grade 3 peripheral neuropathy or persistent Grade 2 peripheral neuropathy may be discontinued for up to about 7 days, and then reduced to a dose of about 2 mg/m$^2$ upon recovery to Grade 1 or 2. In another embodiment, the dosage administered to a patient portraying a persistent Grade 2 peripheral neuropathy, even after receiving a reduced dose, may be discontinue for up to 7 days, and then reduced to dose of 1.825 mg/m$^2$, or a dose of 1.5 mg/m$^2$.

The dosage of VSLI is determined by calculating the body surface area (BSA) of the subject according to well-known methods. For example, according to Mosteller's formula in which the BSA equals the square root of product of the weight of the subject in kg times the height in cm divided by 3600. The "normal" BSA in humans is generally taken to be 1.7 m$^2$ but also depends on other factors including the age and gender of the individual. For example:

Average BSA for adult men: 1.9 m$^2$

Average BSA for adult women: 1.6 m$^2$

Average BSA for children (9 years): 1.07 m$^2$

Average BSA for children (10 years): 1.14 m$^2$

Average BSA for children (12-13 years): 1.33 m$^2$.

(Mosteller R D. Simplified calculation of body-surface area. N Engl J Med 1987; 317:1098)

Example 1

VSLI In Vitro Release Assay Procedure

The following optimized in vitro assay procedure was used to determine the concentration of vincristine released from Vincristine Sulfate Liposomes Injection, 0.16 mg/mL (VSLI) in the presence of 1-Butanol, following ultrafiltration with a Microcon Centrifugal Filter Device.

Procedures for handling and disposal of anticancer drugs must be strictly followed (NIOSH Alert: Preventing occupational exposure to antineoplastic and other hazardous drugs in healthcare settings. 2004. U.S. Department of Health and Human Services, Public Health Service, Centers for Disease Control and Prevention, National Institute for Occupational Safety and Health, DHHS (NIOSH) Publication No. 2004-16; OSHA Technical Manual, TED 1-0.15 A, Section VI: Chapter 2. Controlling Occupational Exposure to Hazardous Drugs. OSHA, 1999; American Society of Health-System Pharmacists. ASHP guidelines on handling hazardous drugs. Am J Health-Syst Pharm. (2006) 63:1172-1193; Polovich M, White J M, Kelleher L O (eds.) 2005. Chemotherapy and biotherapy guidelines and recommendations for practice (2nd. ed.) Pittsburgh, Pa.: Oncology Nursing Society).

Reagents

Albumin, Bovine, Fraction V

Sodium Azide

Sodium Phosphate Dibasic Heptahydrate

Sodium Chloride

Methanol, HPLC grade

Water, USP purified

Diethylamine o-Phosphoric Acid, reagent grade

Polyethylene glycol (PEG) MW 8000, or equivalent

USP Vincristine Sulfate RS (United States Pharmacopeia Reference Standard), USP Cat. No. 714007

1 N Hydrochloric Acid, reagent grade

1-Butanol 99.8%, or equivalent

Tri-Sodium Citrate Dihydrate

Citric Acid Anhydrous

Helium Gas (Praxair), or equivalent

Equipment

Automatic pipettor 100-1000 µL and pipette tips (Eppendorf) or equivalent     Analytical balance (Mettler XS205 or equivalent)

Top loading balance (AND FX2000 or equivalent)

Shaker-Waterbath capable of heating to 37.0°±0.1° C. and shaking at 70 rpm (Julabo model SW23 or equivalent)

Digital timer, Mini-Alarm, NIST traceable (Fisher Scientific or equivalent)

Basic Tray for Shaker-Waterbath (Fisher Scientific or equivalent)

Spring Clamps for 100 mL flasks pH meter (Accument AR25 or equivalent)

pH electrode (Accument AccuTupH or equivalent)

Vacuum System, Buchi Model B-169 (Beckman Instrument) or equivalent Eppendorf centrifuge model 5415-R or equivalent capable of 12,000×g (11,400 rpm)

Glass Flasks, graduated cylinders, glass funnel

High Performance Liquid Chromatograph (HPLC) System with: Sample Injector, HPLC Pump, UV Detector, HPLC software (Agilent Technologies 1100 Series or equivalent)

C8 HPLC cartridge column, 5 μm particle, 4.6×250 mm (Waters Symmetry C8 Cat No. WAT054245, or equivalent)

C8 HPLC guard column, 5 μm particle, 3.9×20 mm Waters Symmetry C8 Cat No. WAT054250, or equivalent)

Guard column holder (Waters Cat No. WAT046910, or equivalent)

End fittings for cartridge column, (Waters Cat No. WAT037525, or equivalent)

Glass Bottles and caps, 50, 100 and 1000 mL 48 well microtiter plates

Vial racks to accommodate Microcon 1.5 mL filtrate tubes

Mobile phase filtration apparatus including funnel and vacuum flask (Phenomenex Cat. No. AIIO-3315 or equivalent)

Glass Pasteur Pipettes or equivalent

Graduated Cylinders 25 mL, 250 mL, 500 mL, 1000 mL and 2000 mL

Vortex mixer (Baxter Scientific Products Cat No. S8223-1 or equivalent)

Stirrer plate (VWR model 310 or equivalent)

NIST traceable thermometer with accuracy to ±0.05° C.

HPLC vials, 2 mL Amber Robo Vial Marking Spot, 12×32 mm, 9 mm thread (Canadian Life Sciences, Cat No. 32009M-1232A or equivalent)

0.45 μL polyethersulfone (PES) membrane filtration device for aqueous solutions

Centrifugal Filter Devices, 100,000 cutoff (Microcon Ultracell YM-100 or equivalent)

Cotton-Tipped Swabs 0.45 μm PTFE membrane filters for organic HPLC solutions, 47 mm, or equivalent 0.45 μm Nylon membrane filters for aqueous HPLC solutions, 47 mm, or equivalent Solutions Phosphate Buffered Saline (PBS)—20 mM sodium phosphate and 130 mM sodium chloride in USP purified water, pH 7.4 and filtered through 0.45 μm PES filter.

Passivation Solution—5% bovine albumin, Fraction V (BSA), 5% polyethylene glycol (PEG) in PBS, filtered through 0.45 μm PES filter.

Incubation Solution—2.75% 1-butanol in PBS.

Solution Diluent—40% USP purified water and 60% methanol

Citrate Solution—0.254 mol/L citrate in USP purified water and filtered through 0.45 μm PES filter.

Mobile Phase Component A—1.67% v/v diethylamine (DEA) Solution, pH 7.5, filtered through a 0.45 μm Nylon filter.

Mobile Phase Component B—Methanol filtered through a 0.45 μm PTFE filter

Preparation of Filtration Device

The Microcon 1.5 mL filtrate tubes are placed in a vile rack, 600 μL of Passivation Solution are added to each vial, bubbles are removed and the vials capped. Sample reservoirs are placed into a clean microtiter plate and 600 μL of Passivation Solution are dispensed to each reservoir and the plates covered. The vials and plates are then allowed to stand at room temperature overnight (from 15 to 24 hours.).

The Passivation solution is then discarded from all sample reservoirs and filtrate vials used for the assay and the reservoirs and vials are rinsed three times with USP purified water. After excess water is removed, the sample reservoirs are inverted and assembled into the filtrate vials. The assembled devices are placed into the centrifuge so the filtrate vial cap is positioned to the inner left side of each vial, and then centrifuged for 3 minutes at 1500×g (4,000 rpm).

The sample reservoirs are removed from the filtrate vials and reassembled in the upright position into the filtrate vials. The assembled devices are then centrifuged for 3 minutes at 12,000×g (11,400 rpm). The sample reservoirs are then removed from the filtrate vials and placed into a clean microtiter plate, and the filtrate vials into a rack.

To dry the filtrate vials, a clean swab is carefully inserted directly into each filtrate vial to touch the bottom and allowed to stand for 3 to 5 minutes or until all liquid has been absorbed into the swab. The swabs are then removed and disposed.

The sample reservoirs are then assembled into the filtrate vial, and the filter device is closed if not used within 15 minutes. If not used within one hour of drying, the passivated filter device is filled with USP purified water and stored under refrigeration for a maximum of 10 days, and the water is removed prior to use.

Preparation of Standards

Stock A—Vincristine Sulfate Standard Stock Solution in Solution Diluent (0.1 mg/mL)

A 50 mg vial of vincristine sulfate reference standard is opened in a fumehood and allowed to equilibrate to ambient humidity for 30 minutes before weight loss determination and weighing for analysis. The contents of more than one vial of reference standard can be combined for equilibration, provided that they are from the same lot.

Using thermogravimetric analysis, duplicate 10 mg portions of the reference standard are heated at 5° C. per minute between ambient temperature and 200° C. under nitrogen flowing at 40 mL per minute. From the thermograms, the accumulated loss in weight is determined between ambient temperature and a point on the plateau before decomposition is indicated (at about 160° C.).

28.00±5.00 mg of the vincristine sulfate USP reference standard is quantitatively transferred into a 250 mL volumetric flask and adjusted to with Solution Diluent to a concentration of approximately 0.1 mg/mL. The exact concentration is calculated according to the following equation:

$$\text{Vincristine Sulfate (Stock } A)\left(\frac{mg}{mL}\right) = \frac{\left[W(mg) \times \frac{P(\%)}{100} \times \frac{100 - \% \text{ weight loss}}{100}\right]}{Vf(mL)}$$

Where:
W=weighed amount of USP Vincristine Sulfate RS in mg
P=potency of USP Vincristine Sulfate RS
Vf=volume of diluted solution, mL (Vf=250)
% weight loss=determined from thermogravimetric analysis Stock B—System Suitability Stock Solution (0.1 mg/mL Vincristine Sulfate in Solution Diluent A solution containing 11.20±2.50 mg of vincristine sulfate USP reference standard (equilibrated to ambient humidity and tested from weight loss) is prepared in a final volume of 100 mL of Diluent Solution, and the final concentration of vincristine sulfate is calculated as described above.

Stock C—Process Stock Solution (0.1 mg/mL Vincristine Sulfate in Citrate Solution)

A solution containing 11.20±2.50 mg of vincristine sulfate USP reference standard (equilibrated to ambient humidity and tested from weight loss) is prepared in a final volume of 100 mL of Citrate Solution, and the final concentration of vincristine sulfate is calculated as described above.

Vincristine Sulfate Calibration Standard (8 μg/mL Vincristine Sulfate in Solution Diluent)

The calibration standard is prepared by diluting 8 mL of Stock A to final volume of 100 mL with Solution Diluent, and the vincristine sulfate concentration (μg/mL) is calculated according to the following equation:

$$Cstd = \frac{(Vi \times Ci)}{Vf}$$

Cstd=Vincristine sulfate concentration in diluted solution, μg/mL

Vi=Volume of Stock A solution, mL

Ci=Vincristine sulfate concentration in Stock A solution, μg/mL

Vf=Volume of diluted solution, mL

Process Suitability Working Standard (20 μg/mL Vincristine Sulfate in PBS)

Stock C is diluted in PBS to a final concentration of approximately 20 μg/mL vincristine sulfate, and the exact concentration of vincristine sulfate is calculated using the same equation as for the Calibration Standard.

System Suitability Standard (SSS) (4 μg/mL Vincristine Sulfate in Diluent Solution)

Stock B is diluted in Diluent Solution to a final concentration of approximately 4 μg/mL vincristine sulfate, and the exact concentration of vincristine sulfate is calculated using the same equation as for the Calibration Standard.

Preparation of VSLI Test Samples

For each VSLI sample, one hundred milliliters of Incubation Solution in a capped, glass bottle is placed into a shaker water bath equilibrated to 37° C.±0.1° C., and allowed to incubate for approximately one hour at 70 rpm to provide gently shaking for the duration of the incubation period.

Prior to the assay procedure, VSLI samples are equilibrated to room temperature. Each VSLI sample is vortexed and a 5.0 mL aliquot of the VSLI sample is transferred into the 100 mL bottle containing the Incubation Solution using a volumetric pipette. Prior to taking the VSLI sample, the inside walls of the pipette are conditioned by aspirating and expelling the VSLI sample. The final 1-butanol concentration of the Incubation Solution, after the VSLI test sample has been added, corresponds to approximately 2.75% (v/v). Blank samples are prepared using 5.0 mL of PBS in place of VSLI.

After addition of the VSLI, the bottle is inverted approximately five times and returned to the shaker-waterbath and incubated for a total time period of 96 hours. At each each time point, of 0.5 h, 2 h, 4 h, 6 h, 24 h, 48 h, 72 h and 96 h, the bottle containing each VSLI sample or blank sample is removed from the waterbath for a maximum of 2 minutes, and two 0.5 mL aliquots are removed from each sample.

Ultrafiltration Procedure

For the ultrafiltration procedure, each aliquot of the VSLI sample and blank control is transferred into a prepared Microcon sample reservoir in a filtration device and immediately centrifuged at 12,000×g (11,4000) for 30 minutes in a centrifuge set at 20° C. After centrifugation is complete, the filtrate vials, which contain from 400-495 μL of filtrate, are removed from the sample reservoirs. The contents of each filtrate vial is vortexed and approximately 200 μL of filtrate from each vial is transferred into an HPLC vial insert for analysis. The remaining filtrates are stored at 5° C.±3° C. for up to one week.

To evaluate the efficiency of the ultrafiltration process, a process suitability standard (PSS) is prepared by diluting 5.0 mL of the Process Suitability Working Standard with Incubation Solution to a final concentration of about 2 μg/mL vincristine sulfate. Two 0.5 mL aliquots are then removed and subjected to the same ultrafiltration procedure as the VSLI test samples. In addition, approximately 1 mL of the unfiltered PSS into an HPLC vial for analysis to determine the concentration of the vincristine sulfate in the PSS prior to the ultrafiltration procedure.

Preparation of Test Sample for Measurement of Total Vincristine Sulfate

At the 24 hour time of the VSLI sample incubation time course, approximately 25 mL of the incubation sample is transferred to a 50 mL glass bottle and allowed to cool to room temperature for about 60 minutes. Twenty milliliters of the room temperature sample is then transferred into a 50 mL volumetric flask and filled with methanol, and allowed to stand at room temperature for about 30 minutes.

HPLC Procedure

Conditions for HPLC Analysis

Column: Waters Symmetry C8 column, 5 μm, 4.6×250 mm

Guard Column: Waters Symmetry C8

Column Temp.: 35° C.

Detector: UV at 297 nm

Autosampler tray temp: 20° C. or ambient

Injection volume; 40 μL

Flow Rate: 1.0 mL/min

Flow Rate between

Incubation pts >6 hrs: 0.1 mL/min

Isocratic condition: pre-mixed mobile phase comprises of 30% mobile     phase component A and 70% mobile phase component B     Run time: 15 min HPLC Assay The column is installed and equilibrated for at least 30 minutes with pre-mixed mobile phase, or until the baseline is stabilized. Then, 1.0 mL of the System Suitability Standard (SSS) is transferred into a 1 mL glass autosampler vial, capped and loaded into the autosampler. 40 μL of the SSS is injected into the system and the retention time of vincristine sulfate is checked. The typical retention time for vincristine sulfate is 8.7 (±10%) minutes.

One milliliter each of the Solution Diluent (blank), Processed Blank, calibration standard, PSS and SSS samples and the test VSLI samples are then run and collected. On Day 1, the processed blank and the 0.5 h, 5 h, 4 h and 6 h samples are placed in the autosampler and run, followed by an SSS sample and blank. On the start of Day 2, the 24 hr sample and the total Vincristine Sulfate samples are processed and run, bracketed by blank and SSS injections, and so now until the 96 hr sample is run followed by a final SSS sample. The HPLS is allowed to run during the entire sequence but the flow rate can be reduced to 0.1 mL/min between runs. The sequence of injections is listed Table 1.

TABLE 1

Injection Sequence

| No. | Sample | No. of Aliquots | No. of Injections |
|---|---|---|---|
| | Day 1 | | |
| 1 | SSS | N/A | 1 |
| 2 | Blank (Solution Diluent) | N/A | 1 |
| 3 | SSS | N/A | 3 |
| 4 | SSS | N/A | 2 |
| 5 | Calibration Std | N/A | 2 |
| 6 | Blank (processed, see section 5.10) | 1 | 1 |
| 7 | PSS (pre ultrafiltration) | N/A | 2 |
| 8 | PSS (post ultrafiltration) | 2 | 1 |
| 9 | Test Sample 0.5 h | 2 | 1 |
| 10 | Test Sample 2 h | 2 | 1 |
| 11 | SSS | N/A | 1 |
| 12 | Test Sample 4 h | 2 | 1 |
| 13 | Test Sample 6 h | 2 | 1 |
| 14 | SSS | N/A | 1 |
| 15 | Blank (Solution Diluent) | | 1 |
| | Day 2 | | |
| 16 | Blank (Solution Diluent) | N/A | 1 |
| 17 | SSS | N/A | 1 |
| 18 | Test Sample 24 h | 2 | 1 |
| 19 | Total Vincristine Sulfate Sample | N/A | 2 |
| 20 | SSS | N/A | 1 |
| 21 | Blank (Solution Diluent) | N/A | 1 |
| | Day 3 | | |
| 22 | Blank (Solution Diluent) | N/A | 1 |
| 23 | SSS | N/A | 1 |
| 24 | Test Sample 48 h | 2 | 1 |
| 25 | SSS | N/A | 1 |
| 26 | Blank (Solution Diluent) | N/A | 1 |
| | Day 4 | | |
| 27 | Blank (Solution Diluent) | N/A | 1 |
| 28 | SSS | N/A | 1 |
| 29 | Test Sample 72 h | 2 | 1 |
| 30 | SSS | N/A | 1 |
| 31 | Blank (Solution Diluent) | N/A | 1 |
| | Day 5 | | |
| 32 | Blank (Solution Diluent) | N/A | 1 |
| 33 | SSS | N/A | 1 |
| 34 | Test Sample 96 h | 2 | 1 |
| 35 | SSS | N/A | 1 |

The suitability of the HPLC system is checked by evaluating each of the pre-run SSS injections. The acceptance criteria for each individual SSS injection is as follows:
Target retention time: 8.7 min (±10%)
Plate count (USP tangent method): ≥2000
USP tailing factor: ≤2.0
In addition, the relative standard deviation (RSD) for the peak area for replicate SSS injections, pre-run (N=5) and full run (grouped SSS injections) should be ≤2.5%.

The percent recovery from the theoretical concentration for each pre-run SSS injection is calculated vincristine sulfate concentration (μg/mL) for each pre-run SSS injection to three decimal places, and should be between about 95.0-105.0%.

The suitability of the HPLC process is evaluated by determining the average vincristine sulfate (μg/mL) assayed pre-ultrafiltration and the vincristine sulfate concentration in post-ultrafiltration PSS. The recovery of the vincristine sulfate for each post-ultrafiltration PSS is calculated according to the following formula:

% Recovery PSS=(Cpost/Cpr)×100 where:
Cpost=vincristine sulfate concentration following ultrafiltration (μg/mL)
Cpre=average vincristine sulfate concentration prior to ultrafilration (μg/mL)
Deviation from the mean for duplicate injections of pre-filtration PSS samples is calculated to one decimal place according to the following formula:

$$\text{Deviation from mean} = \text{Absolute value}\left[\frac{C_{injection1} - C_{average}}{C_{average}}\right] \times 100$$

where:
$C_{average}$=average vincristine sulfate concentration of injection 1 and injection 2 (μg/mL) The acceptable percent deviation from the mean for duplicate injections of pre-ultrafiltration PSS is ≤2.0%, and the acceptable percent recovery of vincristine sulfate for post-ultrafiltration PSS is between about 95.0-105.0%.

The acceptability of test results is evaluated by calculation of the deviation from the mean between the vincristine sulfate released from replicate test samples at each time point calculated to one decimal point according to the following formula:

$$\text{Deviation from mean} = \text{Absolute value}\left[\frac{C_{aliquot1} - C_{average}}{C_{average}}\right] \times 100$$

where:
$C_{average}$=average vincristine sulfate concentration of aliquot 1 and aliquot 2 (μg/mL) The acceptable percent deviation from the mean (duplicate aliquots) for released vincristine for each time point is ≤10.0%, and the percent deviation from the mean of total vincristine sulfate (duplicate injections) is ≤2.0%.

Calculations of total and released vincristine sulfate are also determined according to the following formula:

$$\text{Released vincristine sulfate}(\%) = \left(\frac{Cf}{Ct \times 2.5}\right) \times 100$$

where,
Cf=mean vincristine sulfate concentration from two filtrate aliquots (μg/mL)
Ct=mean vincristine sulfate concentration from duplicate injections of total vincristine sulfate test sample (μg/mL)
2.5=ratio dilution factor between total and released vincristine sulfate Example 2

Optimization of In Vitro Release Assay for VSLI

A number of release media were initially screened and 1-butanol in PBS was selected for further optimization.

Figure 1:
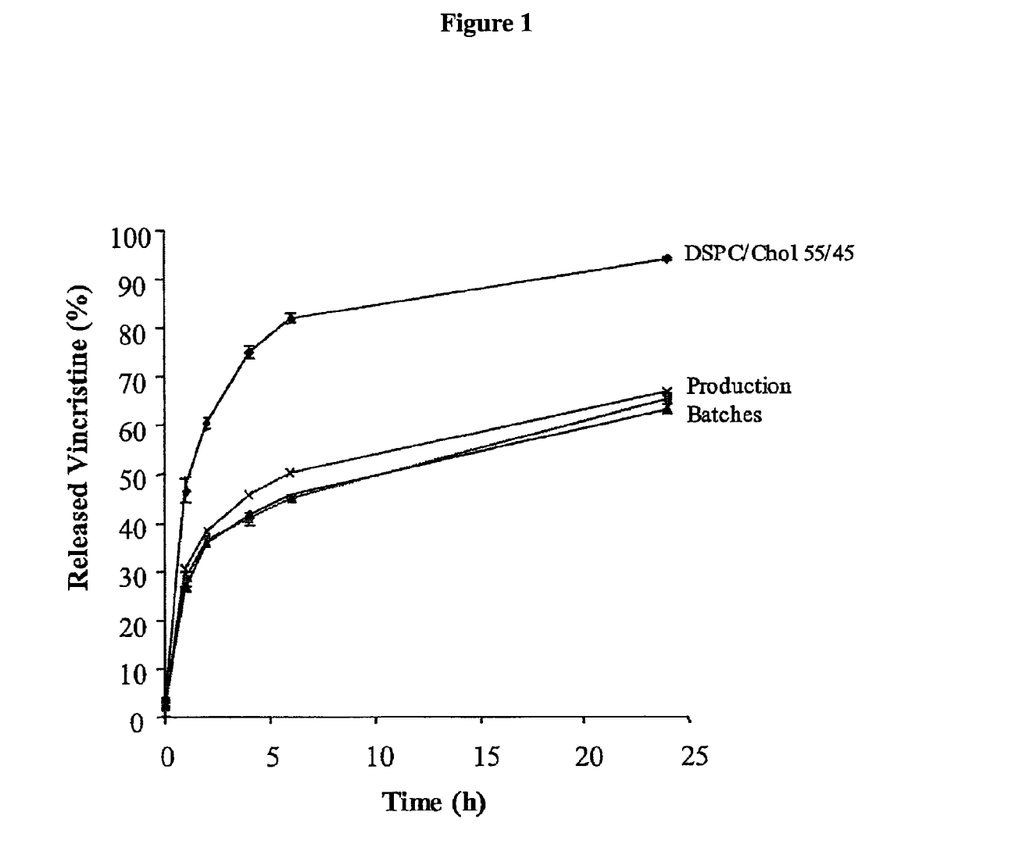
FIG. 1 is a graph demonstrating that the IVR assay using 2.75% 1-butanol in PBS as a release medium for different liposome compositions. DSPC/Chol=distearoylphophatidylcholine/cholesterol; SM/Chol=sphingomyelin/cholesterol.
Figure 2:
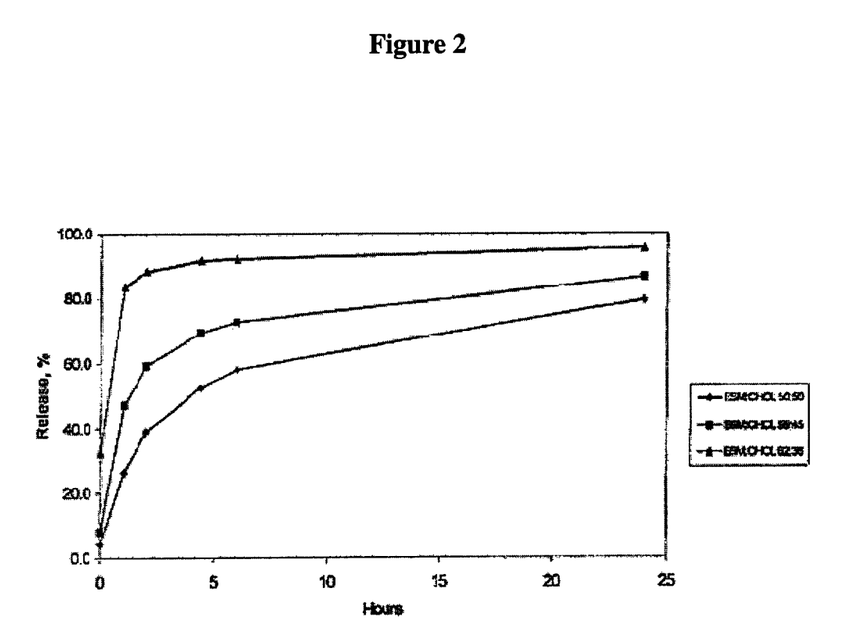
FIG. 2 is a graph demonstrating that the IVR method using 1-butanol in PBS as a release medium can discriminate over a range of SM/Chol ratios. ESM(SM)/Chol=sphingomyelin/cholesterol.

As shown in FIG. 1, the IVR method utilizing 1-butanol in PBS as a release agent is able to discriminate between the DSPC/Chol liposomes and three production batches of SM/Chol liposomes as early as the 1-hour time point. This discriminatory power was maintained throughout the assay. Butanol in (PBS) was also shown able to discriminate over a range of SM/Chol lipid ratios (36-50 mol % cholesterol) (FIG. 2).

Figure 3:
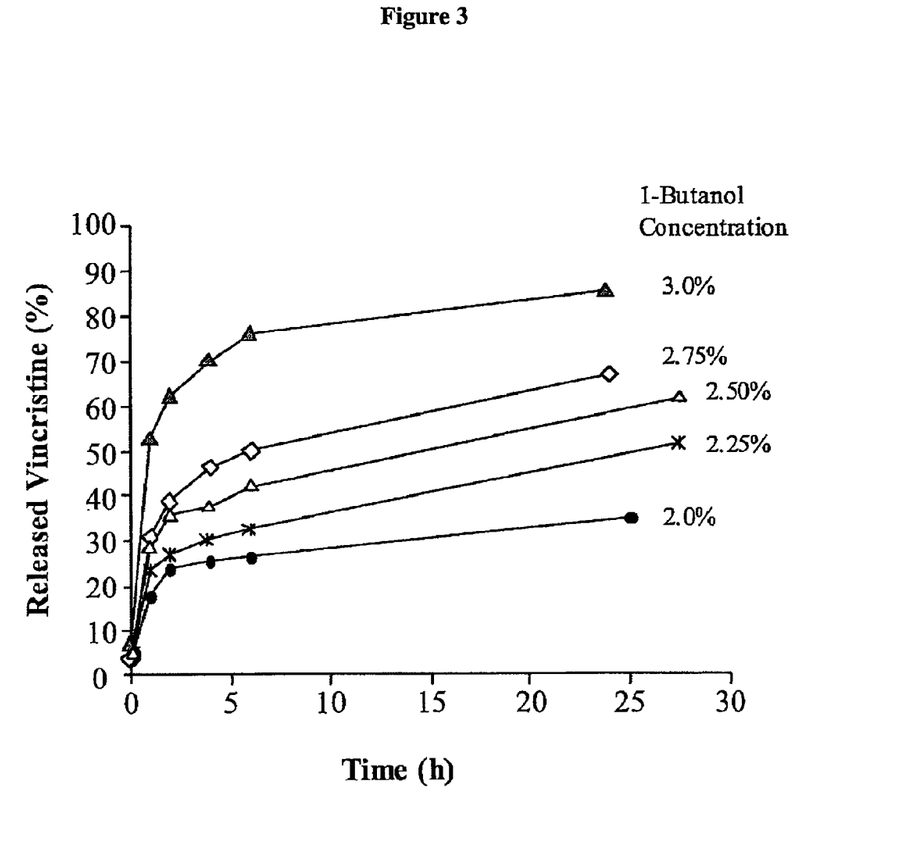
FIG. 3 is a graph depicting the effect of different concentrations of 1-butanol in PBS on the release rate of vincristine from VSLI.

Vincristine release profiles were evaluated in medium containing 1-butanol concentrations of 2.0, 2.25, 2.5, 2.75 and 3.0% (FIG. 3). Over a concentration range of 1-butanol from 2.70 to 2.80% there was minimal impact on the IVR profiles. The f2 values for the 2.70 and 2.80% versus the 2.75% 1-butanol concentration were 85 and 95 respectively, implying equivalence between the curves. A concentration of 2.75% was selected as it provided good discrimination between liposomes with varying liposomes SM/Chol compositions and a good range of drug release over a 24-hour period.

The pH of the release medium was also evaluated over a pH range of 7.0 to 7.4. A higher release profile was observed at pH 7.0 than at 7.4. To provide better control at the onset of vincristine release, and for greater physiological relevance, a pH of 7.4 (±0.01) was chosen for the final IVR assay conditions.

The IVR profiles from the samples incubated at 36 and 37° C. were indistinguishable ($f_2$=83). However, at an incubation temperature of 38° C. the IVR rate was faster and reached a higher level of percent released vincristine compared to 37° C. The $f_2$ value for comparing the profiles at 37 and 38° C. was 52. The low $f_2$ value indicates that water bath temperature is a critical parameter that requires adequate control during routine testing of VSLI.

To optimize separation of free (released) vincristine from encapsulated vincristine prior to HPLC analysis several commercially available ultrafiltration devices were evaluated for the ability to maximize vincristine recovery and ease of use. During this evaluation, various passivation solutions were examined for the ability to block nonspecific binding of vincristine to the surface of the filter membrane in the ultrafiltration device. It was determined that filters pre-treated overnight (15-24 hours) at room temperature with a passivation solution containing 5% bovine serum albumin and 5% polyethylene in PBS, and rinsed prior to use resulted in vincristine recoveries of ≥95%. Of the devices tested, the Microcon YM-30 (30,000 MW cut-off) and the Microcon YM-100 (100,000 MW cut-off) showed excellent vincristine recoveries (>97%) and minimal holdup volume (<2%).

The HPLC analysis used in the IVR assay is based on the USP assay method for VSI. Initial studies determined that an increased injection volume and a reduced flow rate were required to accommodate for the low concentration of vincristine in the release medium, but column temperature, and different lots of columns have no significant impact on the response or percent released vincristine.

Studies were also performed to optimize the VSLI concentration in the release medium by evaluating vincristine recovery, release rate, release profile, and total release. At a 1:10 dilution of VSLI:release medium, the release profile was flatter and the absolute level of release was about 10 to 20% lower than for a 1:20 dilution. Sample preparation was also more difficult at the 1:10 dilution due to increased blockage of the filtration membrane. The vincristine release profile was improved at a 1:20 dilution, while still providing adequate recovery of vincristine. Over dilution negatively impacts the ability of the HPLC/UV assay to detect released vincristine at the lower portion of the concentration range. The dilution of VSLI in release medium was adjusted in the final IVR method to 1:21 to simplify incubation solution preparation.

In summary, the optimization studies demonstrated that the IVR method has unique dependencies on 1-butanol concentration and incubation temperature.

Example 3

Validation of IVR Procedure

The IVR procedure was evaluated for specificity, linearity, accuracy, precision, limits of detection and quantitation, robustness and reproducibility.

Data from a number of assays run using routine HPLC parameters is summarized in Table 2.

TABLE 2

| System Suitability Checks | | |
|---|---|---|
| Item | Range | Acceptance Criteria |
| RSD of peak area | 0.356-1.280 | ≤2.5% |
| Retention time | 8.4-8.8 min | 8.7 (±10%) min |
| Plate count (USP Tangent) | 7576-9620 | ≥2000 |
| Tailing factor (USP) | 1.035-1.158 | ≤2.0 |
| SSS (first five injections) | Recovery = 96.9-102.6% RSD = 0.2-0.7% | Recovery 90.0-110.0% RSD ≤2.5% |

Specificity

The specificity of a method is the ability to assess unambiguously the analyte in the presence of other expected components. Analysis of the vincristine peak in the presence of formulation excipients, sample matrix, and partially degraded VSLI demonstrated adequate resolution and purity of the vincristine peak as defined by Agilent software (Rev. A.08.03), a statistical method for the automated comparison of spectra. The peak purity was determined to be ≥999.9 indicating that there was no co-elution of another peak with the vincristine peak demonstrating that the method is stability indicating, and is specific for the determination of in vitro release of vincristine.

Linearity

Figure 4:
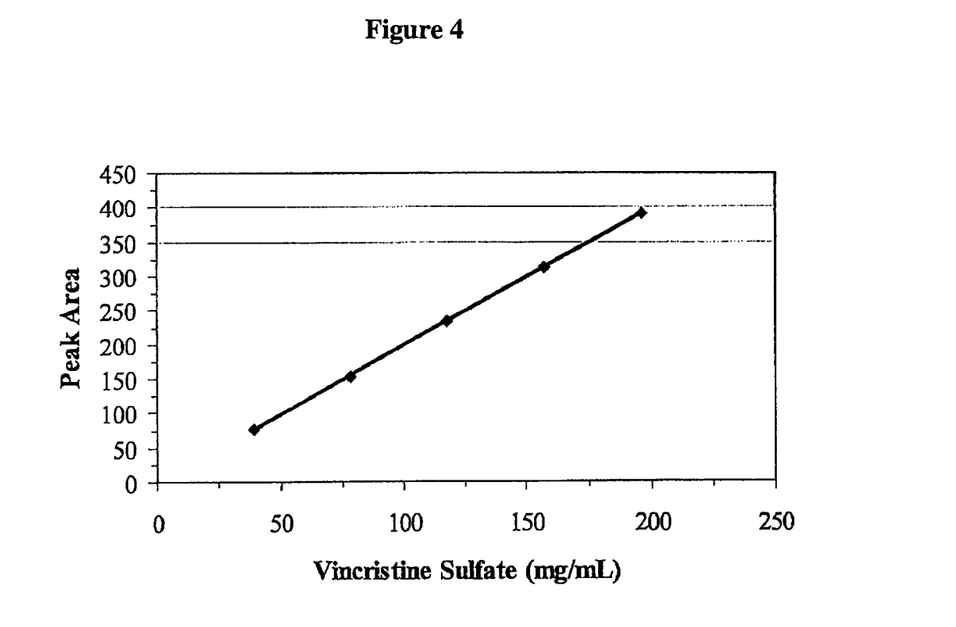
FIG. 4 is a graph depicting the linearity of the IVR for released vincristine.

The linearity of a method is the ability of the method to achieve results that are directly proportional to the concentration of the analyte. The assay procedure was evaluated to establish the range over which the quantitation of the released (free) vincristine is linear. Linearity was evaluated by the coefficient of determination ($R^2$) for the standard curve measuring peak area in response to vincristine concentration. The peak area response of the linearity samples (average of 3 aliquots) was plotted against the concentration of vincristine (FIG. 4). The results demonstrated linearity over the tested range of released vincristine, with a near zero intercept.

Accuracy

The accuracy of a method is the closeness of the determined value with either a conventional true value or a reference value. The accuracy of the IVR assay was determined by analyzing mock samples of VSLI that contained varying, but defined amounts of released (free) vincristine sulfate. The results demonstrated that the method is accurate over the range of 0-125% vincristine concentrations (100%=160 μg/mL).

Precision

The precision of a method is the closeness in agreement between a series of measurements. The repeatability (within assay variations) was determined using the results obtained from the accuracy analyses of the mock samples and from the analysis of a VSLI sample. The relative standard deviation (RSD) of the results was determined to be ≤1% over the range of vincristine concentrations (acceptance criterion ≤10%).

The RSD between VSLI samples for each time point evaluated by the same analyst on the same day was determined to be ≤5% demonstrating acceptable intermediate precision (within laboratory precision; acceptance criterion ≤15%).

The reproducibility (e.g., inter-laboratory precision) of the IVR assay was demonstrated by determining the deviation from the mean for the results obtained from two analysts for the same VSLI samples, and for results obtained from the use of different HPLC instruments. The results indicated a deviation of ≤1% for both analyses (acceptance criterion ≤15%).

Range

The range of the assay method is defined as the lowest to the highest concentrations of vincristine, inclusive, that can be measured with acceptable linearity, recovery, and precision. The method was demonstrated to be capable of measuring total vincristine concentrations in the range of 38.7-199.2 µg/mL (actual concentration), corresponding to 25-125% of the total vincristine sulfate in VSLI. The method has demonstrated to be capable of measuring released vincristine concentrations in the range of 39.2-200.7 µg/mL (actual concentration), corresponding to 25-125% of the total vincristine sulfate in VSLI.

Limits of Detection and Quantitation

The study established the limits of detection and quantitation (LOD and LOQ) by measuring a series of dilutions of a vincristine sulfate reference standard solution. Signal and noise were determined by manual measurement from the chromatograms. The LOD was determined to be 0.037 µg/mL. This corresponds to 0.5% of the target concentration of total vincristine in incubation solution (7.6 µg/mL). The LOQ was determined to be 0.116 µg/mL.

The execution of the validation procedure confirms the method has suitable statistical perspective attributes to be used as a tool for quality control. The assay can be used to assess conformance of a batch to pre-determined criteria at time of manufacture and to assess the long-term Stability and release of the active ingredient. This assay can also assist in quality control for certain scale-up and post-approval changes.

Example 4

Determination of Remaining Encapsulated Vincristine Sulfate

Figure 5:
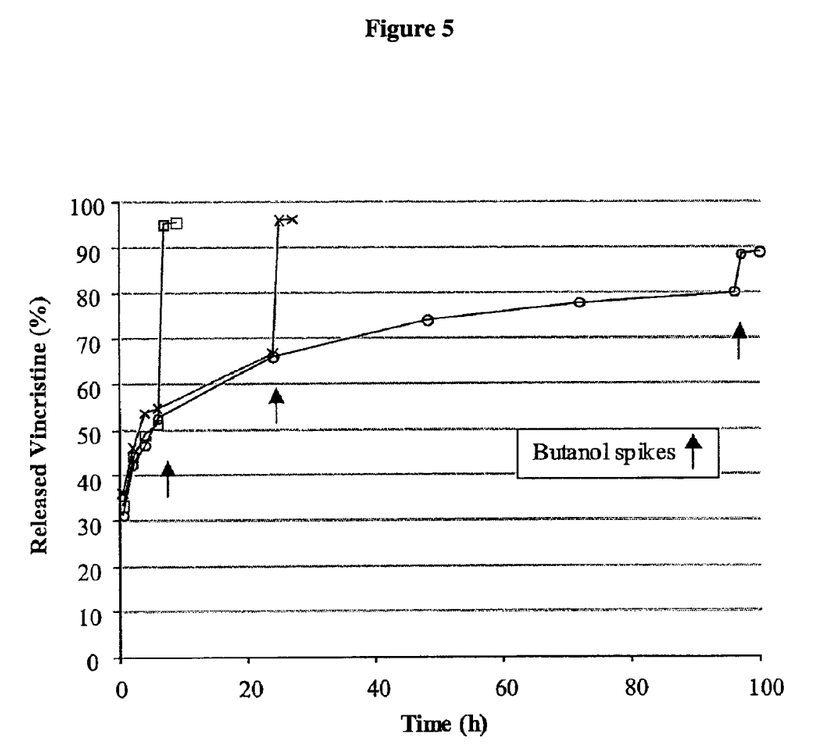
FIG. 5 is a graph depicting the released vincristine from VSLI spiked with 4% 1-butanol.

To determine the amount of vincristine that remains encapsulated, VSLI incubation samples were spiked with additional 1-butanol to induce maximum drug release. The VSLI samples constituted from a single production lot of SCLI were prepared and incubated according to the IVR method, but at the 6-, 24- or 96-hour time points, additional 1-butanol was added to reach a 4% final concentration (FIG. 5).

After spiking at 6 and 24 hours, approximately 96% release of vincristine was observed. However, after spiking at 96 hours, only 89% release was measured. Validation of the IVR method showed that losses through the ultrafiltration device account for approximately 3% of the initial vincristine content. Thus the corrected release values for samples spiked at 6 and 24 hours demonstrate mass balance, while the sample spiked at 96 hours would represent 92% released vincristine.

Since vincristine degrades in neutral aqueous solution at 37° C., the extent of vincristine degradation was evaluated in the IVR samples at each incubation time point. Assaying for vincristine-related compounds in the IVR samples confirmed the presence of N-desformylvincristine, a specified degradant, and an unidentified degradant RC-VCR-02, which increased from 0 to 4% of the peak area over the 96-hour time course. Due to the low vincristine concentration in the IVR samples, these were the only degradant peaks observed above the LOQ.

The mass balance of the 96-hour sample in this spiking experiment was therefore determined as follows: 92% of total vincristine was accounted for as a combination of released (80%), encapsulated—released by the 1-butanol spike (9%), and lost through ultrafiltration (3%). Degradation of vincristine accounted for at least half of the outstanding 8%. Thus the observed 80% released vincristine in the 96-hour sample actually demonstrates >80% release.

SUMMARY

These studies demonstrate that the in vitro release method described herein is suitable use as a routine analytical procedure to monitor the quality and performance of VSLI.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of determining the in vitro release rate of vincristine from vincristine sulfate liposome injection (VSLI), the method comprising the steps of:
   a. adding VSLI to an incubation solution comprising 1-butanol and phosphate buffered saline (PBS), wherein the concentration of 1-butanol after addition of the VSLI is between about 2.7% and about 2.8% (v/v);
   b. heating the incubation solution containing the VSLI for at least about 72 hours at about 37° C.±0.1° C.;
   c. removing an aliquot of the incubation solution containing the VSLI at two or more time points;
   d. separating the released vincristine from the VSLI by filtering each aliquot through a membrane which retains particles with $D_{25}$ of 70 nm and $D_{90}$ of 170 nm separate; and
   e. determining the amount of released vincristine in the filtrate of each aliquot removed at each time point by high performance liquid chromatography,
   wherein the difference in the amount of released vincristine at each time point is indicative of the release rate of vincristine from the VSLI.

2. The method of claim 1, wherein the concentration of 1-butanol in the incubation solution is 2.75%.

3. The method of claim 1, wherein the VSLI is diluted by about 1:21 in the incubation solution.

4. The method of claim 1, wherein the pH of the incubation solution is between about 7.0 and about 7.4.

5. The method of claim 1, wherein the pH of the solution is about 7.4.

6. The method of claim 1, wherein the incubation solution is equilibrated to 37° C.±0.1° C. prior to the addition of the VSLI.

7. The method of claim 1, wherein the incubation solution is heated for about 96 hours.

8. The method of claim 1, wherein the nominal molecular weight limit of the membrane is between about 30,000 and 100,000 daltons.

9. The method of claim 1, wherein the aliquot is filtered at a centrifugal force of about 12,000×g for about 20 to about 30 minutes at 20° C.

10. The method of claim 1, wherein the membrane is pretreated with a passivation solution comprising bovine serum albumin, polyethylene glycol and PBS.

11. The method of claim 1, wherein the VSLI comprises a concentration ratio of about 0.1/1.0 to about 0.2/2.0 vincristine sulfate to lipid.

12. The method of claim 1, wherein the concentration of vincristine sulfate in the VSLI is about 0.1 mg/mL to about 0.5 mg/mL.

13. The method of claim 1, wherein the liposomes in the VSLI comprise between about 75/25 mol %/mol sphingomyelin/cholesterol to 30/50 mol %/mol % sphingomyelin/cholesterol.

14. The method of claim 1, wherein the liposomes in the VSLI comprise approximately 55/45 mol %/mol % sphingomyelin/cholesterol.

15. The method of claim 1, wherein the liposomes have a mean diameter of about 90-125 nm.

* * * * *